United States Patent [19]
Nakano et al.

[11] Patent Number: 4,611,562
[45] Date of Patent: Sep. 16, 1986

[54] METHOD AND SYSTEM FOR INTERNAL COMBUSTION ENGINE OXYGEN SENSOR HEATING CONTROL WHICH PROVIDE SENSOR HEATING LIMITED FOR RELIABLE OPERATION

[75] Inventors: Jiro Nakano; Takao Ishibashi; Takao Akatsuka; Masao Kawaguchi, all of Toyota, Japan

[73] Assignee: Toyota Jidosha Kabushiki Kaisha, Toyota, Japan

[21] Appl. No.: 666,470

[22] Filed: Oct. 30, 1984

[30] Foreign Application Priority Data

May 7, 1984 [JP] Japan .................................. 59-90680

[51] Int. Cl.$^4$ ...................... F02M 7/00; G01N 27/46
[52] U.S. Cl. .................................... 123/440; 123/489; 204/425; 204/426
[58] Field of Search ...................... 123/440, 489, 589; 204/424, 425, 426, 427, 428, 429

[56] References Cited

U.S. PATENT DOCUMENTS

| 4,332,225 | 6/1982 | Cox et al. | 204/424 X |
| 4,356,065 | 10/1982 | Dietz | 204/1 T |
| 4,464,244 | 8/1984 | Uchida et al. | 204/425 |
| 4,500,412 | 2/1985 | Takahashi et al. | 204/425 |

FOREIGN PATENT DOCUMENTS

| 0069690 | 6/1977 | Japan . | |
| 0013396 | 1/1979 | Japan . | |
| 0021393 | 2/1979 | Japan . | |
| 0130650 | 10/1981 | Japan . | |
| 0139657 | 8/1982 | Japan | 204/426 |
| 0200646 | 12/1982 | Japan . | |
| 0083251 | 5/1983 | Japan . | |
| 0105056 | 6/1983 | Japan . | |

Primary Examiner—Willis R. Wolfe, Jr.
Attorney, Agent, or Firm—Kenyon & Kenyon

[57] ABSTRACT

An internal combustion engine has an exhaust system and an oxygen sensor fitted to the exhaust system including a sensor element and an electrically powered heater for heating the sensor element. A method is disclosed for controlling the power supplied to said heater by restricting it to be less than a predetermined value. This restriction may be done by controlling the value of a relatively steady current flowing through said heater, or alternatively may be done by supplying an intermittent voltage to said heater and by controlling the duty factor of said intermittent voltage. The power supplied to said heater may be determined by detecting the current flowing through said heater, or may be determined by detecting the voltage across said heater and the current flowing through said heater. Thereby, during engine heating up operation, the temperature of the heater element is raised as quickly as practicable, without any risk of over quick heating of the heater occurring, which might lead to damage thereto. Accordingly it is ensured that engine performance and the quality of exhaust gas emissions at the time of such engine warming up operation are good. A system is also described for implementing this method.

14 Claims, 13 Drawing Figures

METHOD AND SYSTEM FOR INTERNAL COMBUSTION ENGINE OXYGEN SENSOR HEATING CONTROL WHICH PROVIDE SENSOR HEATING LIMITED FOR RELIABLE OPERATION

BACKGROUND OF THE INVENTION

The present invention relates to a method of controlling the heating of an oxygen sensor fitted to the exhaust system of an internal combustion engine for the purpose of controlling air-fuel mixture air/fuel ratio, and to a system for practicing the method. More particularly, the present invention relates to such a method and device for oxygen sensor heating control which limit the current passing through and the power dissipated in a resistive electrical heater element of the oxygen sensor, so as to ensure that the heater element is not damaged by too great a thermal shock.

It is known to fit an oxygen sensor to the exhaust system of an internal combustion engine. Such an oxygen sensor typically comprises a solid electrolyte or semiconductor, and varies a generated current or resistance in response to the concentration of oxygen in the exhaust gases of the engine. This electrical signal is fed to a control device which controls the amount of fuel provided to the engine in relation to the amount of air sucked thereinto, and is used for controlling the air/fuel ratio of the air-fuel mixture supplied to the engine by a feedback process. Various such forms of control device, which practice various methods of air-fuel mixture rtio control, are per se known.

The output of the sensor element of such an oxygen sensor varies with temperature, and, particularly when the air/fuel ratio is weak and is in the range of 14.5 to 25, in order for the sensor element to accurately measure the oxygen concentration, said sensor element must be maintained at a temperature higher than a certain critical minimum active temperature. This maintenance of the temperature of the sensor element can be done by using a heater, and oxygen sensors with sensor element heaters have already been proposed, along with methods for operation of such heaters; for example in Japanese Patent Application No. 53-78476, which has been published as Japanese Patent Publication No. 54-13396.

Further, in Japanese Patent Application No. 53-83120, which has been published as Japanese Patent Publication No. 54-21393, there has been proposed a method and a system for control of the electrical power supplied to such an oxygen sensor element heater, in which the power is varies as a function of intake manifold pressure, of throttle opening, and of engine revolution speed, so as to ensure that the oxygen sensor element is kept at a temperature no lower than its minimum active temperature.

The sensor element of such an oxygen sensor fitted to an exhaust system is of course heated up by the exhaust gases in the exhaust system, so the effect of a heater for the sensor element must be controlled to take account of the temperature of these exhaust gases. Now, in an internal combustion engine which is controlled by a throttle valve, the exhaust temperature is largely determined by the amount of air-fuel mixture supplied per engine piston stroke and by engine revolution speed, and if the air/fuel ratio of the air-fuel mixture is constant the amount of such mixture supplied is proportional to the rate of intake air flow. Therefore, in the above mentioned patent applications, the above are used as parameters, and the supply of electricity to the sensor element heater is varied depending on the engine load and the engine revolution speed. Thus, the exhaust temperature is considered to depend on the engine intake flow and engine revolution speed, and the values are determined experimentally in advance with reasonable accuracy. This method and system are adequate to keep the temperature of the sensor element of the oxygen sensor reasonably constant regardless of engine operational conditions.

The sensor element of such an oxygen sensor fitted to an exhaust system is of course at a temperature substantially the same as that of the engine as a whole, when the engine has not been running for any substantial time. Now, the heater element is typically of a pure resistive load type, using the Joule heating phenomenon for producing heating power, and typically such a heater element has a resistance which increases as its temperature increases. In other words, since the heater element is usually designed in view of its use when at its normal operating temperature, its resistance when cold, i.e. when the engine is cold, is relatively rather low. Thus, when the engine is first started up from cold, there is a risk that initially the current through the heater element may be rather large, due to its low resistance, and that thus an unduly high amount of electrical power may be initially dissipated in the heater. If this happens, the resultant rapid rate of heating up of the heater element may cause a thermal shock which is bad for the endurance of the heater element. In the case of, for example, a platinum resistor on an alumina mount, which is a fairly typical type of heater element for this sort of application, sudden rises in temperature caused by such unduly high power dissipation in the heater element may cause thermal stress and overheating of the material of the heater element, which can lead to agglomeration of this heater material which can in its turn cause a discontinuity to arise in the circuit; or thermal stress on the mount of the heater element may cause it to be broken. All these problems affect the reliability of the heater element.

In Japanese Patent Application No. 56-203678, which has been published as Japanese Patent Publication No. 58-105056, the suggestion has been made to limit the initial voltage supplied to the heater element, so as to restrict the power dissipation therein in the initial phase of engine operation. However, in this prior art, this is suggested to be done from the time that the heater is switched on, which is determined from the state of the switch controlling the heater, and thus the voltage supplied to the heater element is restricted in all cases irrespective of the actual temperature of or of the resistance of the heater element, and in every instance of starting up, irrespective of whether the engine is cold or warm when it is being started up, and accordingly sometimes the heater element voltage is restricted when this is not necessary, as during warm restarting. This is means that the restriction of the heater voltage for the purpose of limiting surges cannot be kept to a minimum.

An alternative solution, proposed in Japanese Patent Application No. 56-181531, which has been published as Japanese Patent Publication No. 58-83251, is to delay energizing the heater element until the oxygen sensor and its heater have been somewhat heated up by the exhaust gases of the engine, so that the resistance of the heater element has been somewhat increased. But this involves waiting for the exhaust gases to warm up the heater element, and delays use of the heater element for properly warming the oxygen sensor element, which delays starting the feedback control of the air/fuel ratio of the air-fuel mixture.

SUMMARY OF THE INVENTION

Accordingly, it is the primary object of the present invention to provide a method and system for internal combustion engine oxygen sensor heating control, which limit the power level fed to the sensor element heater so as to limit the rate of the temperature rise of the element of said heater.

It is a further object of the present invention to provide such a method and system for oxygen sensor heating control, which only limit said power level for the sensor element heater when it is necessary to do so, thus minimizing such limiting action.

It is a further object of the present invention to provide such a method and system for oxygen sensor heating control, which heat the oxygen sensor element up from the engine starting condition at substantially the maximum practicable safe speed, in substantially all engine operating conditions.

It is a yet further object of the present invention to provide such a method and system for oxygen sensor heating control, which provides good initial performance of the engine during its warming up operational phase, by warming up the sensor element of the oxygen sensor as quickly as safely practicable.

It is a further object of the present invention to provide such a method and system for oxygen sensor heating control, which do not risk overheating the heater element of the oxygen sensor heater.

It is a further object of the present invention to provide such a method and system for oxygen sensor heating control, which do not place unnecessary stress on the heater element of the oxygen sensor heater.

It is a further object of the present invention to provide such a method and system for oxygen sensor heating control, which do not risk agglomeration of the material of, and consequent electrical discontinuity of, the heater element of the oxygen sensor heater.

It is a further object of the present invention to provide such a method and system for oxygen sensor heating control, which likewise do not risk breakage of a mounting portion of said heater element of said oxygen sensor heater.

It is a yet further object of the present invention to provide such a method and system for oxygen sensor heating control, which maintains the reliability of the heater element of the oxygen sensor heater and of the apparatus as a whole.

It is a yet further object of the present invention to provide such a method and system for oxygen sensor heating control, which minimize the occurrence of the condition that during initial engine warming up operation the quality of the exhaust emissions of the engine should be poor.

According to the most general method aspect of the present invention, these and other objects are accomplished by, for an internal combustion engine comprising an exhaust system and an oxygen sensor fitted to said exhaust system comprising a sensor element and an electrically powered heater for heating said sensor element: a method for controlling the electrical supply to said heater, wherein: the power supplied to said heater is restricted to be less than a predetermined value; and according to the most general device aspect of the present invention these and other objects are accomplished by, for an internal combustion engine comprising an exhaust system and an oxygen sensor fitted to said exhaust system comprising a sensor element and an electrically powered heater for heating said sensor element: a system for controlling the electrical supply to said heater, comprising: a means for detecting the electrical power supplied to said heater; a means for determining a target value for the electrical power supplied to said heater and for ensuring that it is less than a certain predetermined value; and a means for controlling the electrical power supplied to said heater to be substantially equal to said target value.

According to such a method and such a system, the power dissipated by said heater is restricted to be no more than a certain predetermined value, thus preventing surging and avoiding the problems outlined above of overheating of the heater element, as well of unnecessary stress on it, and of agglomeration of its material and consequent electrical discontinuity. Also, risk of breakage of a mounting portion of said heater element of said oxygen sensor heater is avoided. Thus, the reliability of the heater element of the oxygen sensor heater and of the apparatus as a whole is maintained. The power supply to the oxygen sensor heater either may be controlled by varying a substantially steady current passing through said heater, as by a transistor for example, or may be controlled dynamically by varying the duty factor of a voltage supplied to the heater. Further, if as is preferable the power supplied to said heater is determined by detecting the current flowing through said heater, and if it is assumed that the voltage supplied to said heater (i.e. from the vehicle battery) is substantially constant, as a first approximation, then it becomes possible to perform the restriction of the power being dissipated by said heater element, substantially only when necessary and substantially only to the minimum extent required, and by doing this the oxygen sensor element is heated up from the engine starting condition at substantially the maximum practicable safe speed, in substantially all engine operating conditions. Thus, this method and system provide good initial performance of the engine during its warming up operational phase, by warming up the sensor element of the oxygen sensor as quickly as safely practicable. Accordingly, it is as much as possible prevented that during initial engine warming up operation the quality of the exhaust emissions of the engine should be poor. For yet more positive avoidance of heat surge problems, it is preferable to derive data relating to the power supplied to said heater by detecting the voltage being supplied across said heater as well as the current flowing through said heater, and in this case the power being dissipated by the heater can be positively determined, in either of the ways outlined above.

BRIEF DESCRIPTION OF THE DRAWINGS

The present invention will now be shown and described with reference to the preferred embodiments thereof, and with reference to the illustrative drawings. It should be clearly understood, however, that the description of the embodiments, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and features are denoted by like reference symbols in the various figures thereof; and:

DESCRIPTION OF THE PREFERRED EMBODIMENTS

Figure 1:
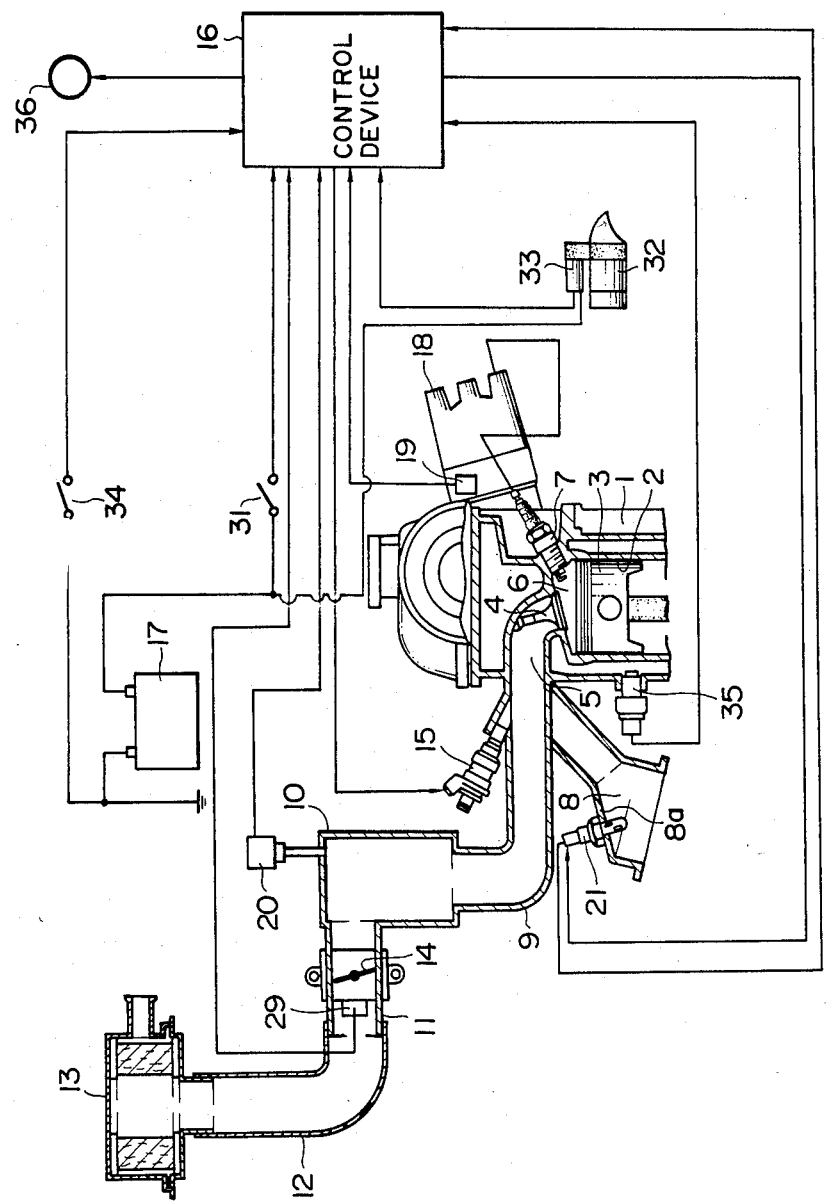
FIG. 1 is a partly schematic partly sectional view of an internal combustion engine which is equipped with the first preferred embodiment of the oxygen sensor heating control system of the present invention, also showing various ancillary elements thereof.

FIG. 1 shows in schematic view an internal combustion engine with an oxygen sensor of the above described kind, said engine incorporating the first preferred embodiment of the oxygen sensor heating control system of the present invention, for performing the first preferred embodiment of the oxygen sensor heating control method of the present invention. In this figure, the internal combustion engine 1 has a cylinder bore 2 within which a piston 3 reciprocates, said piston 3 being coupled in a per se conventional manner to a crankshaft, not shown, by a connecting rod, only partially shown; in fact the engine 1 has a plurality of such cylinders and pistons but only one of each of them can be seen in the figure. A combustion chamber 6 is defined above the piston 3 in the figure in the cylinder bore 2, between it and a cylinder head, and an intake port 5 opens to this combustion chamber 6 via a valve aperture the opening and closing of which is controlled by an intake valve 4. A per se conventional spark plug 7 provides ignition for air-fuel mixture in the combustion chamber 6 when appropriately energized. Further, an exhaust port, not shown in the figure, opens to the combustion chamber 6 via a valve aperture the opening and closing of which is controlled by an exhaust valve, also not shown, and to this exhaust port there is connected an exhaust system, only a portion of an exhaust manifold 8 incorporated in which is shown.

To the inlet port 5 there is connected the downstream end of an intake manifold 9, the upstream end of which is connected to the outlet of a surge tank 10. To the inlet of the surge tank 10 there is connected the downstream end of a throttle body 11, the upstream end of which is connected to the downstream end of an inlet tube 12. The upstream end of this inlet tube 12 is communicated to the outlet of an air cleaner 13, the inlet of which is left open to the atmosphere. In the throttle body 11 there is mounted an intake butterfly valve 14 the opening and closing action of which for intake air amount control is linked to the foot depression movement of a throttle pedal for the engine 1, not shown, by a throttle pedal linkage also not shown.

To the intake manifold 9 there is mounted a per se conventional fuel injection valve 15 which incorporates a solenoid 15a (not shown in FIG. 1), and this fuel injection valve 15 is supplied with pressurized fuel (i.e. gasoline) by a fuel supply system which is not shown. The opening and closing action of this valve 15 is electronically controlled by a control device 16 which will be more particularly described hereinafter. Thus, the valve 15 squirts spirts of fuel into the intake manifold 9 the total volume of each of which depends on the opening and closing times thus provided for said fuel injection valve 15 by the control device 16.

The control device 16 is supplied with actuating electrical energy from the battery 17 of the vehicle to which this engine 1 is fitted, via an ignition switch 31. To the distributor 18 of the engine 1 there is fitted a crank angle sensor 19, the electrical output signal of which is representative of the position of the crankshaft of the engine 1 and is dispatched to the control device 16. To the surge tank 10 of the engine 1 there is fitted an intake pressure sensor 20, the electrical output signal of which is representative of the air pressure in the intake system of the engine 1 and is also dispatched to the control device 16. To the wall 8a of the exhaust manifold 8 of the engine 1 there is fitted an oxygen sensor 21 to be more particularly described later, the electrical output signal of which is representative of the oxygen concentration in the exhaust gases flowing through said exhaust manifold 8 and is also dispatched to the control device 16; and the oxygen sensor 21 further has a heater 28 as will be described later, supply of actuating electrical energy to which is provided from the control device 16. To the throttle valve 14 mounted in the intake system of the engine 1 there is fitted a throttle valve idling opening amount sensor 29 incorporating a switch 29a (not shown particularly in FIG. 1), the electrical output signal of which is also dispatched to the control device 16 and is representative of the opening amount of said throttle valve 14, being ON when said throttle valve 14 is opened by more than a predetermined amount and thus indicating engine operation at a level higher than idling level and being OFF when the throttle valve 14 is opened by less than said predetermined amount and thus indicating engine idling operation. To the starter 32 of the engine 1 there is fitted a starter switch 33, an electrical output signal from which is indicative of whether said starter 32 is being actuated to crank said engine 1 or not and is also dispatched to the control device 16. And to the water jacket of the engine 1 there is fitted a water temperature sensor 35, the electric output signal of which is indicative of the temperature of the cooling water of said engine 1 and is also dispatched to the control device 16. Further, a test switch 34 optionally provides earthing for a terminal of the control device 16, and an output signal from said control device 16 is fed to a test alarm lamp 36.

Figure 2:
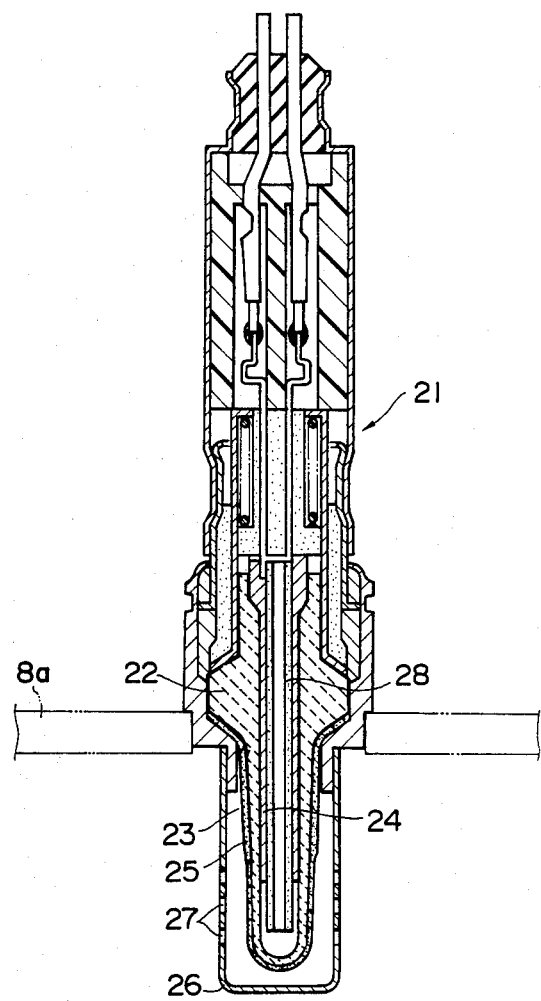
FIG. 2 is a longitudinal sectional view of an oxygen sensor fitted to the engine of FIG. 1 and shown in said figure.

Referring to FIG. 2, the oxygen sensor 21 fitted in the wall 8a of the exhaust manifold 8 comprises a sensor element 22 formed as a tube with one end closed and made of a solid electrolyte material such as zirconia which can transmit oxygen ions. The outside of this sensor element 22 has, laid on it, an outer electrode 23 formed as a porous thin conducting layer (this layer is not clearly separately shown in the figure because it is so thin as to be represented by a single line), and the inside of said sensor element 22 has, likewise laid on it, an inner electrode 24 likewise formed as a porous thin conducting layer (again, this layer is shown only by a single line in FIG. 2). The outer surface of the outer electrode 23 has an exhaust gas dispersion layer 25 also laid on it, said layer 25 being formed of porous ceramic. The sensor element 22, etc., are mounted within a casing and so on, not particularly described here because they are per se known, and are fixed into the wall 8a of the exhaust manifold 8 with their lower parts in FIG. 2 projecting into the interior of said exhaust manifold 8. And a shield 26 with a plurality of holes 27 formed therein is provided around said lower ends of the sensor element 22 etc. projecting into the exhaust manifold 8, so as to protect them from the impact of the rushing flow of exhaust gases in the exhaust manifold 8, while allowing said exhaust gases to impinge gently on the exhaust gas dispersion layer 25 and the outer electrode 23 to reach the sensor element 22. During use of this oxygen sensor 21 as a current limiting type lean sensor, a certain voltage is applied by the control device 16 between the outer electrode 23 and the inner electrode 24, so that the current between these electrodes increases approximately in proportion to the oxygen concentration in the exhaust gases flowing through the exhaust manifold 8, within certain limits, as is per se well known. And, in order to keep the sensor element 22 etc. at the correct temperature for activation, an electrical heater 28 is provided for the oxygen sensor 21. This heater 28 is a per se known type of resistive heater, and the magnitude of the heating power instantaneously provided thereby is proportional to the product of the voltage and the amperage being provided by the control device 16 thereto.

The function of the control device 16 is in partial outline as follows. From the data it receives relating to engine rotational speed from the crank angle sensor 19 and relating to intake manifold pressure from the intake manifold pressure sensor 20, it determines the volume of intake air which is being sucked into the combustion chamber in each intake stroke of the piston 3, and according thereto determines a theoretically proper amount of fuel to be mixed with this intake air to provide a proper and appropriate target value for the air/fuel ratio of the air-fuel mixture in the combustion chamber. And, during normal engine operation when the engine 1 has been warmed up as is indicated by the output of the engine cooling water temperature sensor 35, based upon the actual value of the oxygen concentration in the exhaust gases in exhaust manifold 8 of the engine 1 as detected by the oxygen sensor 21, information regarding which is dispatched therefrom to the control device 16, said control device 16 makes a correction to this theoretical value in order to produce a value for the actual amount of fuel to be injected, so as to bring the air/fuel ratio to its target value by a form of per se known feedback control. Then, the control device 16 produces electrical output signals at appropriate crank angles and supplies them to the solenoid 15a of the fuel injector 15, so as to control the opening and closing of the fuel injector 15 so as to inject this determined appropriate amount of fuel, in each injection spirt. On the other hand, when the engine 1 has not yet properly been warmed up as is again indicated by the output of the engine cooling water temperature sensor 35, no such feedback correction according to exhaust oxygen concentration of the calculated theoretically proper amount of fuel to be injected in order to provide a proper and appropriate target value for the air/fuel ratio of the air-fuel mixture in the combustion chamber is made, but instead the theoretically calculated value is directly used as a value of fuel to be injected, and accordingly the control of fuel injection is by a form of open loop control without any feedback. At this time the air/fuel ratio is controlled to be smaller than in the warmed up engine case when feedback is being utilized.

Figure 3:
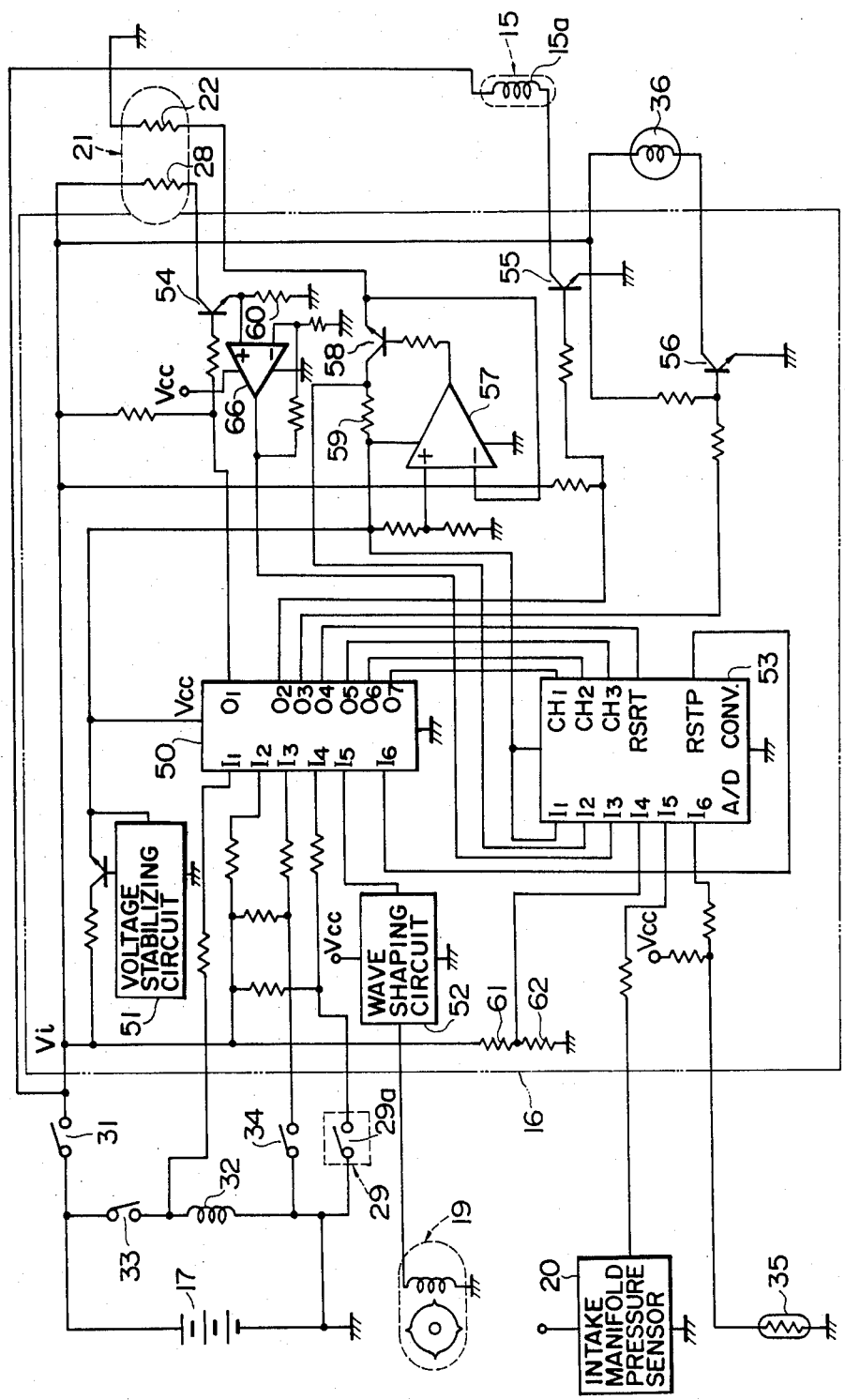
FIG. 3 is a partial circuit diagram of the first preferred embodiment of the oxygen sensor heating control system of the present invention, and of various ancillary elements thereof, and particularly shows a microcomputer incorporated in said control system.

Referring to FIG. 3, herein the internal structure of the control device 16 is partially shown as an electrical circuit diagram, and also ancillary circuits relating thereto are shown. This control device 16 comprises a microcomputer 50, which may be for example of the Motorola 6801 type, and this microcomputer 50 is powered, like other parts of the circuitry of the control device 16, by a constant voltage Vcc supplied by a voltage regulator circuit 51 of a per se well known type, when and only when the ignition switch 31 of the vehicle is ON. This microcomputer 50 of this first preferred embodiment has six inputs designated in the figure as I1 through I6 and seven outputs designated as O1 through O7. The inputs I1 through I6 are connected as follows. The input I1 receives an ON signal when and only when the starter switch 33 is in the ON state. The input I2 receives an ON signal when and only when the ignition switch 31 of the vehicle is in the ON state. The input I3 receives an ON signal when and only when the test switch 34 is in the OFF state. The input I4 receives an ON signal when and only when the switch 29a incorporated in the throttle valve idling opening amount sensor 29 is in the OFF state, i.e. when and only when the engine 1 is not idling. The input I5 receives the output of the crank angle sensor 19, after this has been converted to a square wave by a wave shaping circuit 52. And the input I6 receives a pulse width signal from a RSTP terminal of an A/D converter (an analog-digital converter) 53 of a per se well known sort. Further, the outputs O1 through O7 are connected as follows. The signal from the output O1 is furnished to the base of a transistor 54 as a pulse signal, so as to control the power supplied to the heater 28 of the oxygen sensor 21 as will be explained hereinafter. The signal from the output O2 is furnished to the base of a transistor 55 as a pulse signal, so as to control the solenoid 15a of the fuel injector 15 for providing fuel injection. The signal from the output O3 is furnished to the base of a transistor 56 as a sensor diagnostic result signal, so as to selectively energize the test alarm lamp 36 according to the result of circuit testing, as will be explained hereinafter. The signal from the output O4 is furnished to a convert control terminal RSRT of the A/D converter 53 as a convert start signal. And the signals from the outputs O5 through O7 are furnished as channel control signals to the channel control terminals CH1 through CH3 respectively of said A/D converter 53.

The transistor 54 receives the pulse signal from the output O1 of the microcomputer 50 at its base, and is thereby selectively switched ON so as to provide power via its collector to the heater 28 of the oxygen sensor 21, when and only when said pulse signal from said output O1 is ON. This power for the heater 28 is provided directly from the battery 17 via the ignition switch 31, i.e. not via the voltage regulation circuit 51. The transistor 55 receives the pulse signal from the output O2 of the microcomputer 50 at its base, and is thereby selectively switched ON so as to provide power via its collector to the solenoid coil 15a of the fuel injector 15, when and only when said pulse signal from said output O2 is ON. And the transistor 56 receives the signal from the output O3 of the microcomputer 50 at its base, and is thereby selectively switched ON so as to provide power via its collector to the test alarm lamp 36, when and only when said signal from said output O3 is ON.

And the reference numeral 57 denotes a differential amplifier: when the ignition switch 31 is ON, then a constant voltage Vcc is provided via the voltage regulation circuit 51, and drives the transistor 58 to supply a constant voltage to the sensor element 22 of the oxygen sensor 21.

The A/D converter 53 comprises a multiplexer, not particularly shown, and is powered by the constant voltage Vcc supplied by the voltage regulator circuit 51. This A/D converter 53 of this first preferred embodiment has six inputs designated as I1 through I6, as well as a control terminal RSRT and an output terminal RSTP and channels CH1 through CH3. The inputs I1 through I6 are connected as follows. The input I1 receives the reference voltage signal Vcc. The input I2 receives a voltage signal dropped from this reference voltage Vcc by a variable amount which depends upon the current through the sensor element 22 of the oxygen sensor 21 because of the resistor 59 as shown in the circuit diagram of FIG. 3. The input I3 receives a voltage signal amplified by a differential amplifier 66 from the voltage across a load dropping resistor 60, thus detecting the value of the current passing through the heater 28 of the oxygen sensor 21. The input I4 receives a voltage signal proportional to the current value of the voltage Vi being supplied by the battery 17, according to the operation of a voltage divider circuit incorporating two resistors 61 and 62. The input I5 receives a voltage signal representative of the pressure in the surge tank 10 of the engine intake system from the intake pressure sensor 20. And the input I6 receives a voltage signal representative of the temperature of the cooling water of the engine 1 from the engine cooling water temperature sensor 35.

Thus during operation by using a combination of the CH1 through CH3 signals from the microcomputer 50 a particular one of the input signals I1 through I6 is selected, and then, when the "start A/D convert" signal is dispatched by the microcomputer 50 (from its output O4) and is received at the RSRT terminal of the A/D converter 53, said A/D converter 53 performs the analog-digital conversion process and outputs a pulse width signal corresponding to the voltage of the selected input from its output terminal RSTP to the input I6 of the microcomputer 50. In particular, the microcomputer 50 receives pulse width signals from the A/D converter 53 which are together representative of the voltage across the current detecting resistor 59 for the sensor element 22 of the oxygen sensor 21, said signals being received by said A/D converter 53 at its I1 and I2 input terminals; and, by converting these pulse width signals into digital values and by subtracting one of them from the other, the microcomputer 50 can obtain a digital value representative of said voltage across said sensor element 22. This value, which is representative of the oxygen concentration in the exhaust gases flowing through the exhaust manifold 8, is the value that the microcomputer 50 uses for performing the above described feedback control of the air/fuel ratio of the air-fuel mixture supplied to the engine 1, when appropriate.

Now, the operation of this first preferred embodiment of the oxygen sensor heating control system of the present invention, while performing the first preferred embodiment of the oxygen sensor heating control method of the present invention, will be explained with reference to FIGS. 4, 5, and 6, which are flow charts of the operation of certain parts of the program stored in the microcomputer 50.

Figure 4:
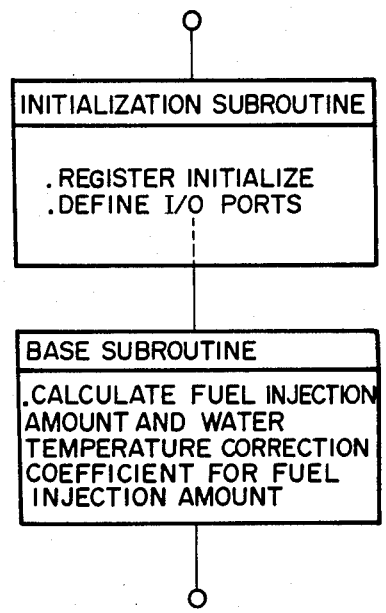
FIG. 4 is a flow chart of an initialization and base subroutine stored in the memory of the microcomputer of FIG. 3 and executed by it during the practice of the first preferred embodiment of the oxygen sensor heating control method of the present invention.

The flow chart of FIG. 4 shows the operation of an initialization and base subroutine which is caused to be executed by the microcomputer 50 when the ignition switch 31 is turned on. The initialization part of this subroutine performs various operations such as register initialization and I/O port definition and so on, while the base part of this subroutine performs various operations such as calculating the fuel injection amount for feedback and the fuel injection amount cooling water temperature correction coefficient and so on.

Figure 5:
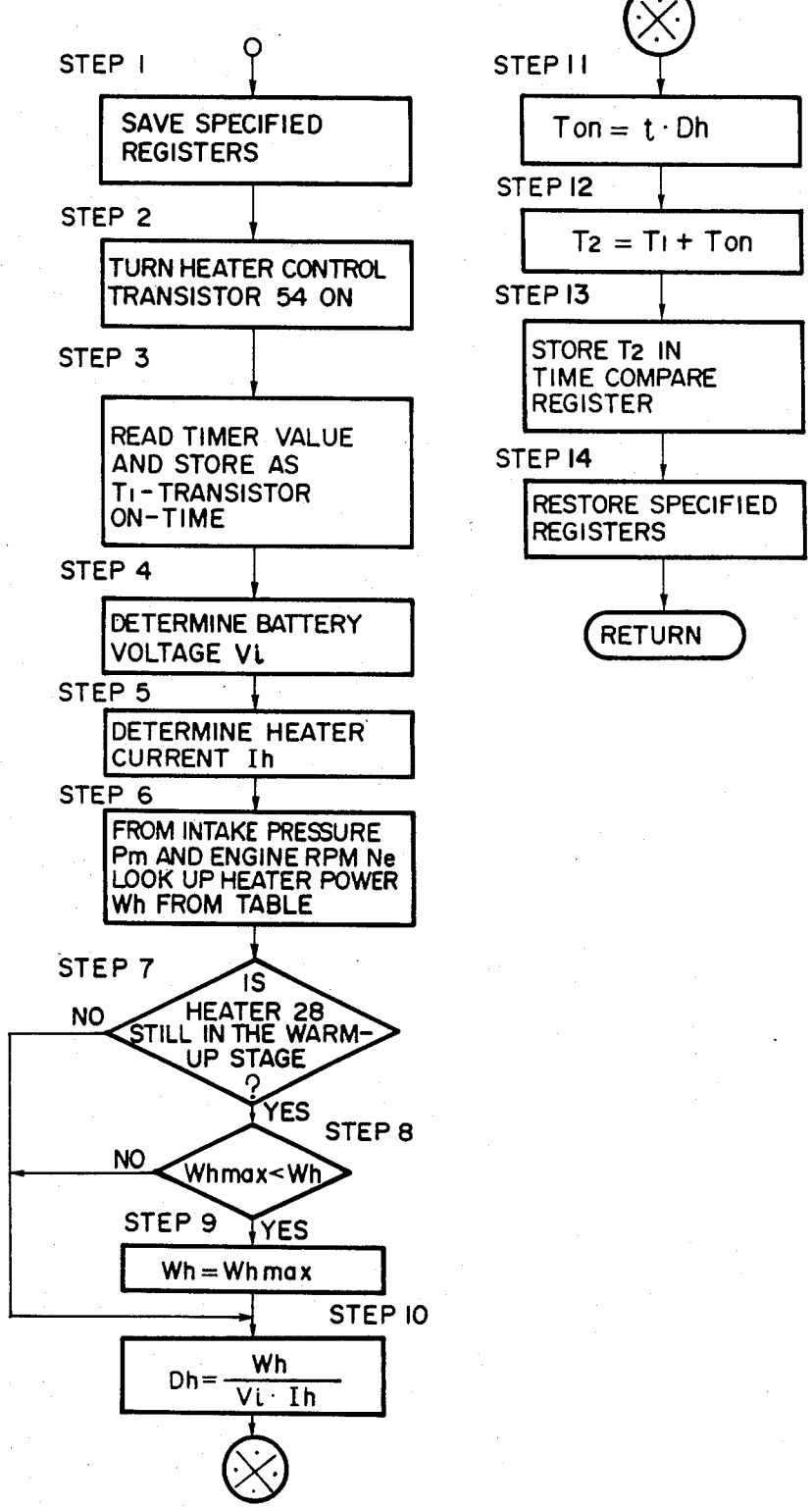
FIG. 5 is a flow chart of an interrupt subroutine for controlling supply of electrical energy to an oxygen sensor heater, stored in the memory of the microcomputer of FIG. 3 and executed by it at fixed intervals during the practice of said first preferred method embodiment.

The flow chart of FIG. 5 shows the operation of an interrupt subroutine for controlling supply of electrical energy to the heater 28 of the oxygen sensor 21; and this subroutine is caused to be executed by the microcomputer 50 at fixed intervals, which are for example of the order of tens of milliseconds.

In this FIG. 5 subroutine, first, in the step 1, certain registers are saved.

Next, in the step 2, the heater control transistor 54 is turned ON, i.e. an ON signal is output to the base of the transistor 54 from the output O1 of the microcomputer 50. This starts to supply power to the heater 28, i.e. turns said heater ON.

Next, in the step 3, the present count value of a free running timer attached to the microcomputer 50 is read, and is stored as T1, the ON time for the transistor 54.

Next, in the step 4, the value Vi of the battery voltage is determined by, as described above, selecting the input I4 of the A/D converter 53 (see FIG. 3), which receives a voltage representative of this battery voltage Vi. In this case, the A/D converter 53 sends an output pulse signal representative of the battery voltage Vi to the microcomputer 50. Also, similarly, in the next step 5, the value Ih of the current through the heater 28 is determined, by selecting the input I3 of the A/D converter 53, and by thus reading into the microcomputer 50 a pulse signal corresponding to the voltage drop across the resistor 60 on said input I3 of the A/D converter 53.

Next, in the step 6, first the current values of the intake manifold pressure Pm and the engine revolution speed Ne are determined by the microcomputer 50: the intake manifold pressure Pm is determined in a similar way to the determination of the battery voltage Vi and of the heater current Ih in the steps 4 and 5 by the microcomputer 50 selecting the input I5 of the A/D converter 53, and the engine revolution speed Ne is determined by calculating the time interval between successive pulses from the crank angle position sensor 19 supplied to the input terminal I5 of the microcomputer 50. Next, by consultation of a two way look up table of values stored in the ROM (read only memory) of the microcomputer 50, a proper and appropriate value for the amount Wh of electrical power to be supplied to the heater 28 of the oxygen sensor 21 is determined. The values of Wh in this look up tablef in the ROM are determined in advance by experiment, and generally decrease as the intake pressure increases and as the engine revolution speed increases.

Next, in the step 7, a test is made as to whether the heater 28 is still in the warming up stage, or not. This may be defined according to any of a variety of criteria: for example, the heater 28 may be considered as still in the warming up stage, if the temperature of the engine cooling water at the start of engine operation was less than a certain value, and also less than a certain time interval has elapsed since said engine starting. If the heater 28 is now fully warmed up (result of decision NO), then the flow of control passes next to the step 10; but if it is not (result of decision YES), control passes next to the step 8.

Next, in the step 8, a test is made as to whether the power Wh which it is proposed to supply to the heater 28 is greater than the maximum permissible or tolerable power level $Wh_{max}$, or not. (This maximum permissible power level $Wh_{max}$ is defined as the product of the average heater current over a fixed interval, $Ih_{mean}$, and the supply voltage Vi). If the heater 28 is not being required to dissipate too much power (result of decision NO), then the flow of control passes next to the step 10; but if it appears that the heater 28 is going to be asked to dissipate excessive power (result of decision YES), then the flow of control passes next to the step 9.

In this step 9, the value of the power Wh to be supplied to the heater 28 is set to be equal to the maximum permissible or tolerable power level $Wh_{max}$. Thus, it is impossible for greater power than the maximum tolerable power level $Wh_{max}$ to be supplied to the heater 28, during the heater warming up stage, by the operation of the test step 8 and of this step 9. Next, the flow of control passes to the step 10.

In this step 10, the duty ratio Dh of the power pulse signal to be supplied to the heater element 28 of the oxygen sensor 21, in order to obtain the correct desired (average) power supply value Wh, is calculated as the ratio of the desired power Wh and the power which would be dissipated in the heater element 28 if a continuous supply of power from the battery 17 were provided thereto—i.e. the product of the battery voltage Vi and the present heater current Ih. This duty ratio Dh decreases with increase in Ih, the current in the heater 28. Next, control passes to the step 11.

Next, in the step 11, from the heater control period t and the duty ratio Dh calculated as above, the length of time Ton that the heater 28 is to be energized is calculated as t.Dh. And next, in the step 12, the time point T2 at which the heater 28 should be deenergized is determined, as being T1+Ton.

Next, in the step 13, this time T2, at which the transistor 54 should be turned OFF and the heater 28 should be deenergized, is stored in a "time compare register".

Finally, in the step 14, the registers which were saved in the step 1 are restored; and then the subroutine returns.

Figure 6:
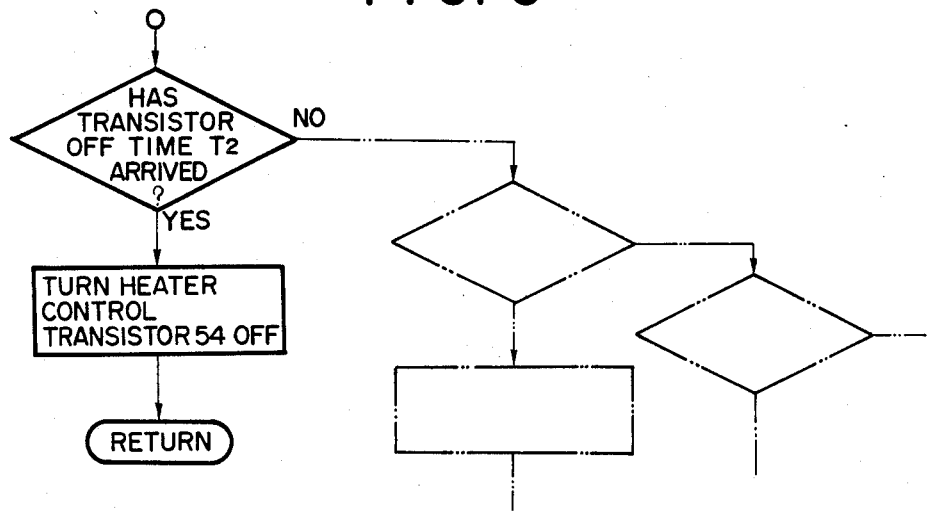
FIG. 6 is a flow chart of a time compare interrupt subroutine also stored in the memory of the microcomputer of FIG. 3 during the practice of said first preferred method embodiment.

The flow chart of FIG. 6 partially shows the operation of a time compare interrupt subroutine. In this subroutine, first a decision is made as to whether the transistor off time T2, stored in the time compare register as explained in the step 13, has arrived or not. It should be understood that the time counter is up-counted at fixed time intervals. If the time point T2 has not yet arrived, then the flow of control is transferred to various other interrupt decisions and actions, as schematically indicated by the double dotted lines and boxes; but, if the time point T2 for switching the heater power supply transistor 54 has in fact arrived, then the flow of control is transferred to a block which turns said heater control transistor 54 OFF by outputting to its base an OFF signal from the output O1 of the microcomputer 50. This stops supplying power to the heater 28, i.e. turns said heater 28 OFF. And then finally the subroutine returns.

Figure 7:
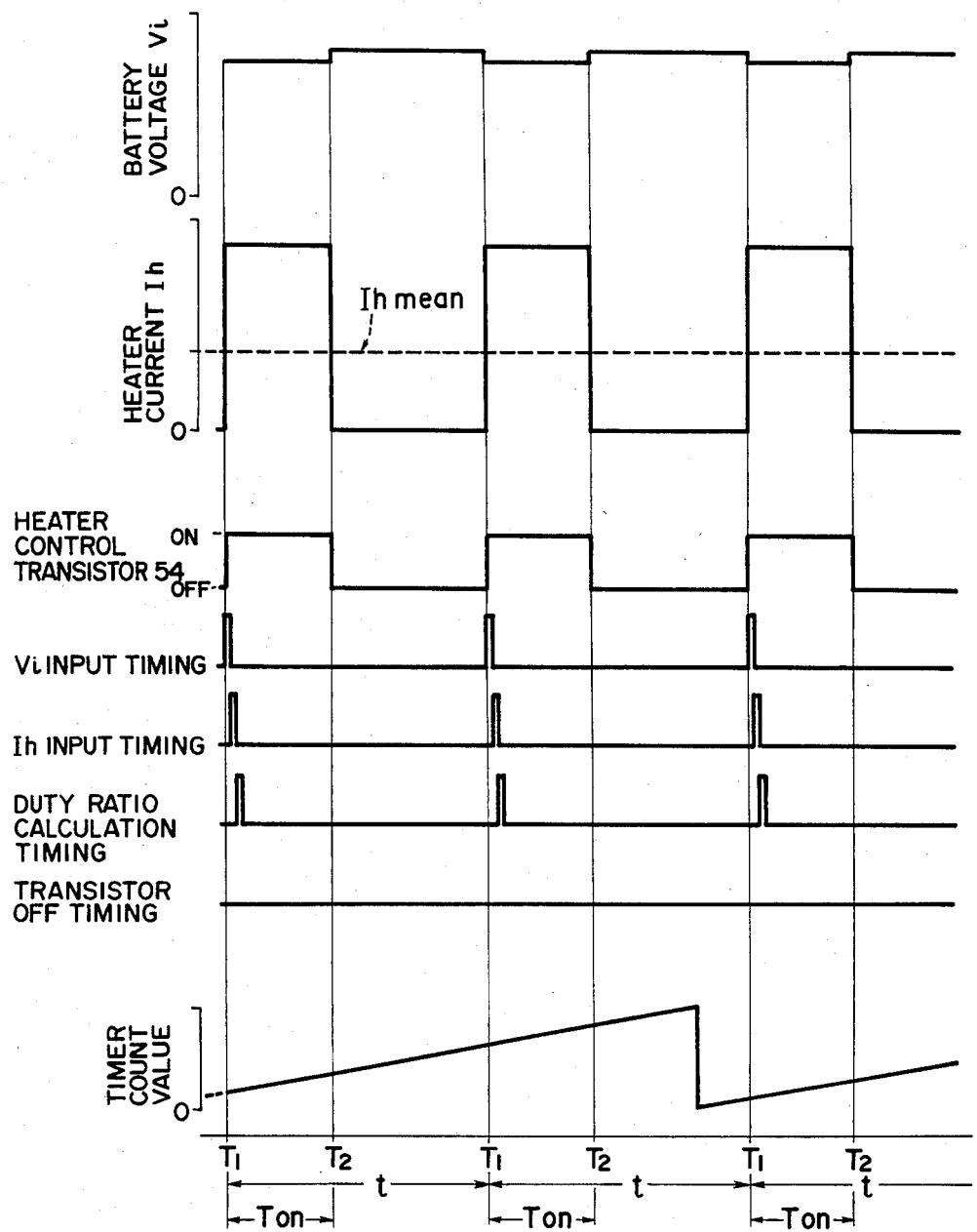
FIG. 7 is a time chart showing, against time, the voltage being delivered by the battery of the vehicle incorporating this system, the current being supplied to the heater for the oxygen sensor element, the ON/OFF signal to a heater control transistor, a voltage input timing, a heater current input timing, the timing of a calculation of duty ratio, the timing of a transistor-OFF signal, and the value of a count C counted by a timer, in the case of this first preferred embodiment of the present invention.
Figure 8:
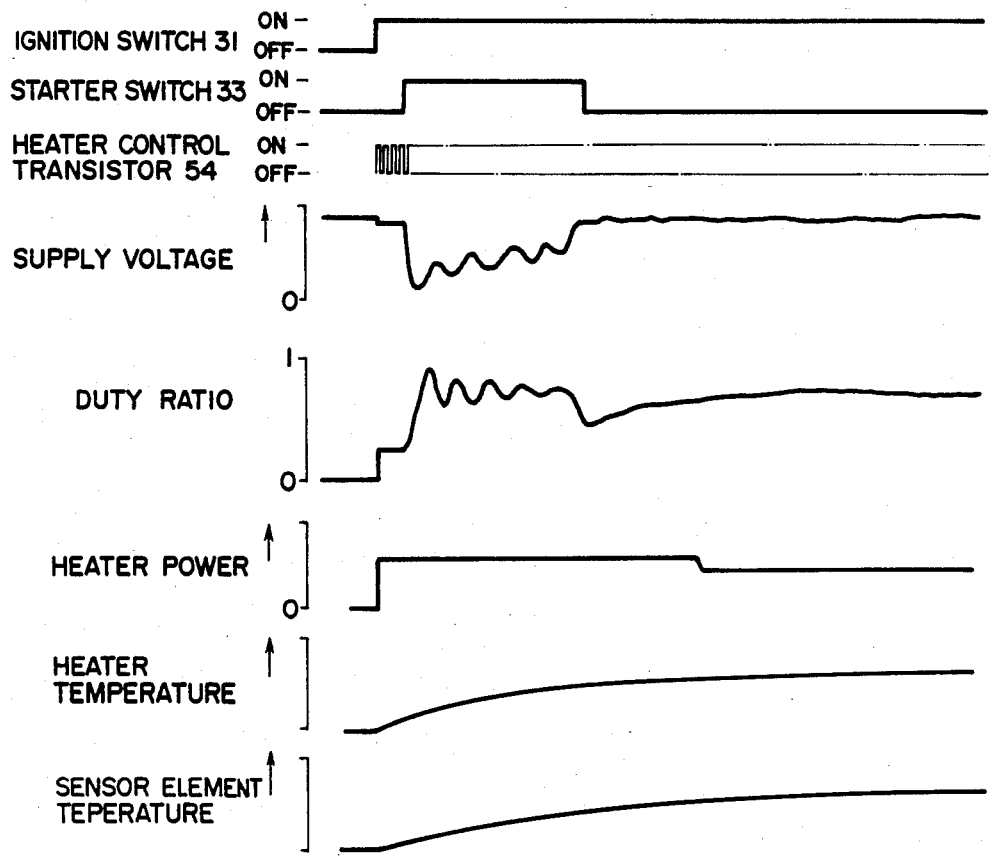
FIG. 8 is a time chart showing, against time, the ON/OFF situation of the ignition switch and the starter switch of the vehicle to which the system of FIGS. 1 through 3 is fitted, the ON/OFF situation of a control transistor for the oxygen sensor element heater, the voltage being delivered by the battery of the vehicle, the duty ratio of a controlling pulse signal to said heater control transistor, the power supplied to said heater, the temperature of said heater, and the temperature of the sensor element of said oxygen sensor.
Figure 9:
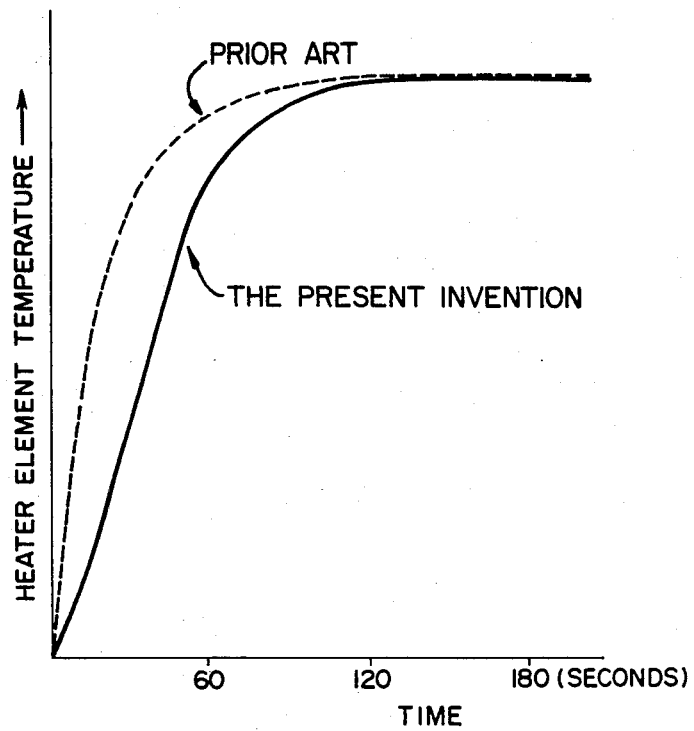
FIG. 9 is a graph showing temperature of the heater element of the oxygen sensor on the vertical axis and time on the horizontal axis, both with regard to the first preferred embodiment of the present invention as shown by the solid line and with regard to a typical prior art as shown by the single dashed line.

Thus, referring to FIG. 7, which is a timing chart showing the duty ratio control performed by the interrupt routine, and which shows against time the battery voltage Vi, the current Ih received by the heater 28, the ON/OFF signal to the heater control transistor 54, the Vi input timing, the Ih input timing, the timing of the calculation of duty ratio, the timing of the transistor-OFF signal, and the count value counted by the timer, the operation of the shown preferred embodiment of the present invention will be further clarified. The results of this operation are further shown by FIG. 8, which is a time chart showing, against time, the ON/OFF situation of the ignition switch 31 and the starter switch 33, the ON/OFF situation of the heater control transistor 54, the voltage being delivered by the battery 17, the duty ratio of the pulse signal to the transistor 54, the power being supplied to the heater 28, the temperature of said heater 28, and the temperature of the sensor element 22 of the oxygen sensor 21. And, referring to FIG. 9, which is a graph showing heater element temperature on the vertical axis and time on the horizontal axis for the present invention by the solid line and for a typical prior art by the single dashed line, it is demonstrated that the heater element 28 is heated up somewhat more slowly by the method and system of the present invention, especially in the earlier part of the warming up process, than by the shown prior art method and system, but reaches its operating temperature not very much slower overall. Thereby thermal stress is effectively avoided. But, as will be seen by consideration of this figure, no unnecessary restriction of the power supplied to the heater element 28 is performed, so that the time to full warmup is only a little longer than in the prior art.

Thus, it is seen that, according to the method and the system of the present invention, the power dissipated by the heater is restricted to be no more than a certain predetermined value, thus preventing surging and avoiding the problems outlined above of overheating of the heater element, as well of unnecessary stress on it, and of agglomeration of its material and consequent electrical discontinuity. Also, risk of breakage of a mounting portion of said heater element of said oxygen sensor heater is avoided. Thus, the reliability of the heater element of the oxygen sensor heater and of the apparatus as a whole is maintained. Further, if as is preferable the power supplied to said heater is determined by detecting the current flowing through said heater, and if it is assumed (as in the shown first preferred embodiment) that the voltage supplied to said heater (i.e. from the vehicle battery) is substantially constant, as a first approximation, then it becomes possible to perform the restriction of the power being dissipated by said heater element, substantially only when necessary and substantially only to the minimum extent required, and by doing this the oxygen sensor element is heated up from the engine starting condition at substantially the maximum practicable safe speed, in substantially all engine operating conditions. Thus, this method and system according to the present invention provide good initial performance of the engine during its warming up operational phase, by warming up the sensor element of the oxygen sensor as quickly as safely practicable. Accordingly, it is as much as possible prevented that during initial engine warming up operation the quality of the exhaust emissions of the engine should be poor.

Figure 10:
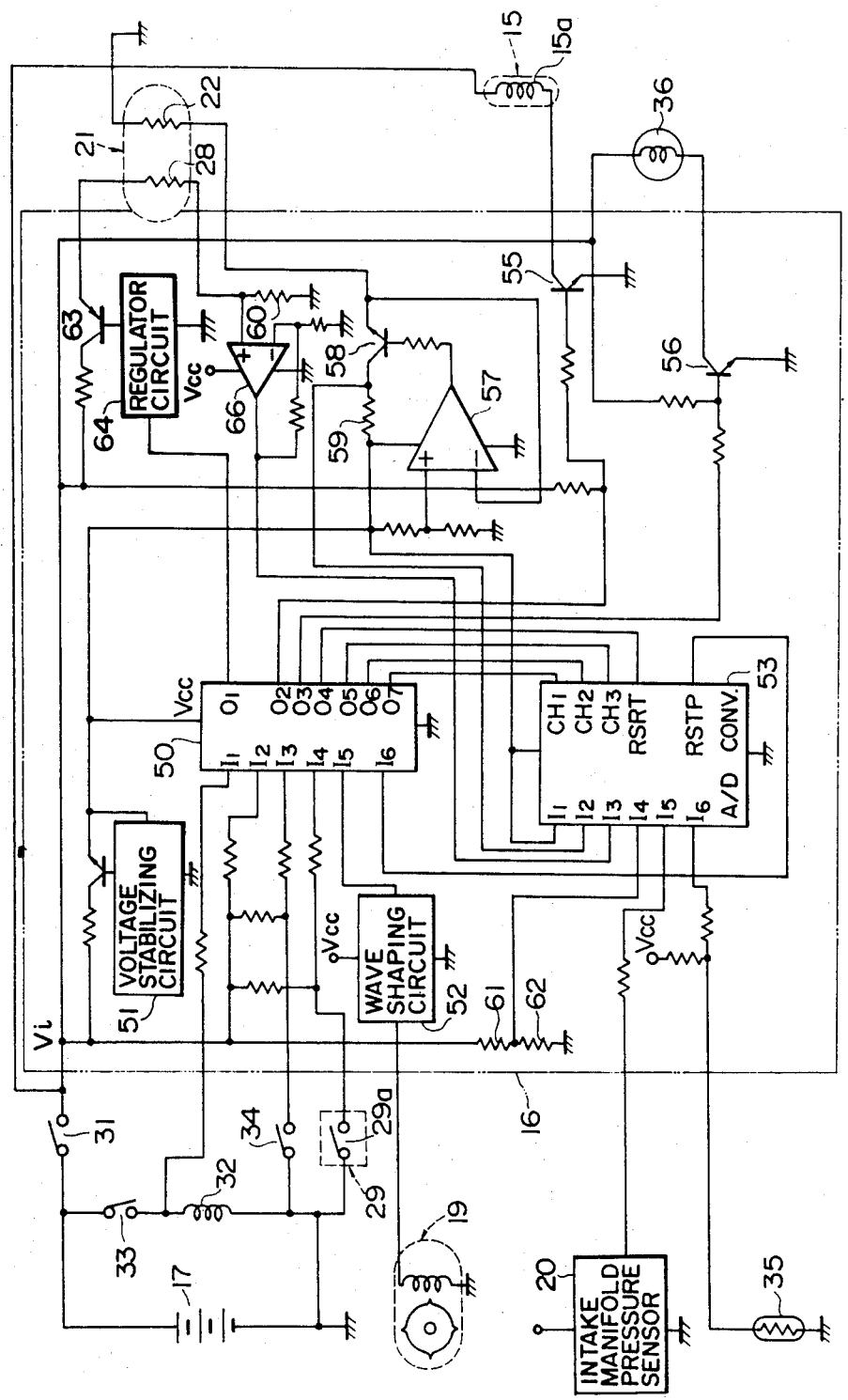
FIG. 10 is, similarly to FIG. 3 for the first preferred embodiment, a partial circuit diagram of the second preferred embodiment of the oxygen sensor heating control system of the present invention, also showing various ancillary parts thereof, in said second embodiment the current to the heater element of the oxygen sensor being continuous and being regulated by a transistor coupled to a regulator circuit, instead of being a duty ratio type current signal outputted from a transistor as was the case in the first preferred embodiment of FIG. 3 etc.

In the above described first preferred embodiment of the present invention, the control of the power to the heater element 28 was performed using duty ratio control, but alternatively this control may be performed by direct control of the heater current. This is done in the second preferred embodiment of the present invention: FIG. 10 shows a partial circuit diagram of the control device 16 of the second preferred device embodiment; and reference symbols in this figure like to the symbols of FIGS. 1 through 3 relating to the first preferred embodiment correspond to like parts of said first preferred embodiment. It will be seen that this circuit diagram differs from the circuit diagram of FIG. 3, only in that the power supply to the heater element 28 is controlled by a transistor 63, the base of which is connected to the output of a regulator circuit 64, which is controlled from the output O1 of the microcomputer 50. Thus, within the operating range of the transistor 63, its base to emitter current controls its collector to emitter current linearly. In other words, the regulator circuit 64 receives a pulse signal from the output O1 of the microcomputer 50 which conveys information by its duty ratio, and produces a voltage signal corresponding to that duty ratio and supplies it to the base of the transistor 63. Otherwise, this second preferred embodiment functions in the same way as the first preferred embodiment, and the same advantages and benefits are obtained, as in the case of said first preferred embodiment described above.

Figure 11:
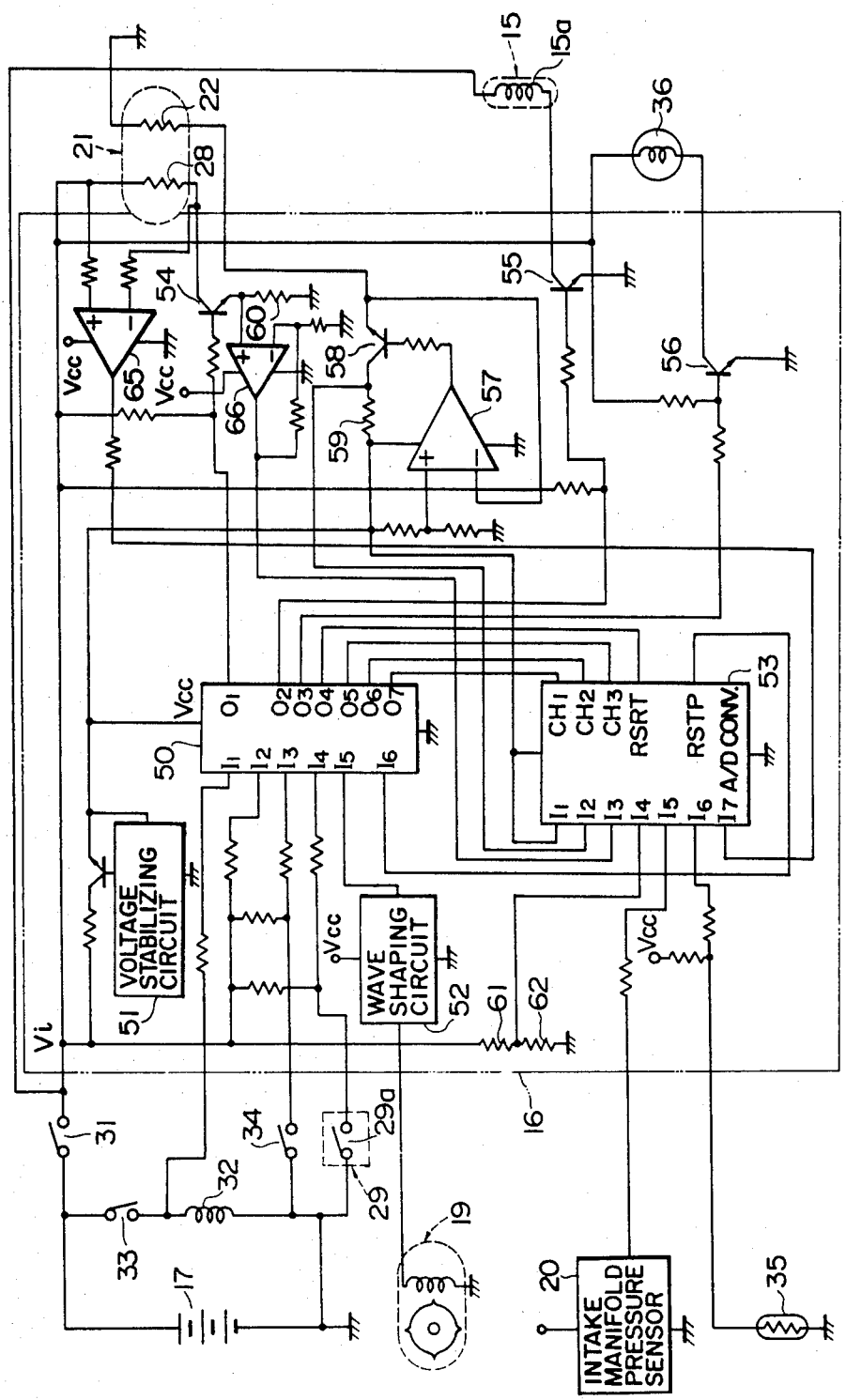
FIG. 11 is, similarly to FIGS. 3 and 10 for the first and second preferred embodiments, a partial circuit diagram of the third preferred embodiment of the oxygen sensor heating control system of the present invention, also showing various ancillary parts thereof, in said third embodiment the voltage applied across the heater element of the oxygen sensor being measured and being fed back to the control microcomputer, as well as the current passing through said heater element.
Figure 12:
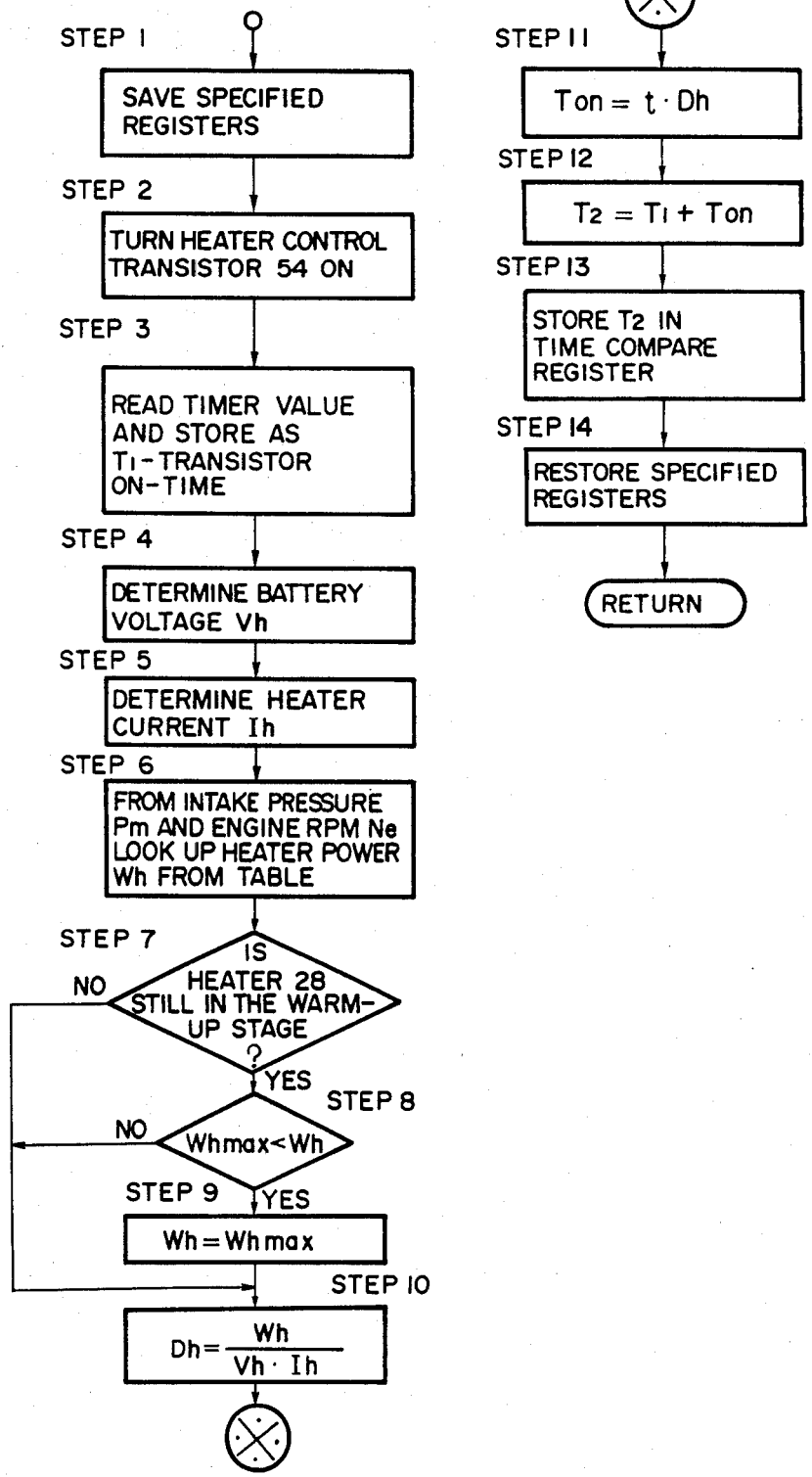
FIG. 12 is, similarly to FIG. 5 for the first preferred embodiment, a flow chart of a subroutine executed by the microcomputer of the third preferred embodiment of the oxygen sensor heating control system of the present invention shown in FIG. 11.

In FIG. 11 there is shown a partial circuit diagram of the control device 16 of a third preferred device embodiment of the present invention; and, again, reference symbols like to those used in FIGS. 1 through 10 correspond to like parts of the first and second preferred embodiments. In this third preferred embodiment, the heater element 28 is driven directly from a transistor 54, as in the first preferred embodiment, but in addition the actual voltage supplied to said heater element 28 is measured by a differential amplifier 65, the output signal of which is sent to the input I7 of the A/D converter 53. The flow chart of the subroutine of the microcomputer 50 in this third preferred embodiment which corresponds to the subroutine of the first preferred embodiment whose flow chart is shown in FIG. 5 is shown in FIG. 12. Corresponding to the variant operation explained above, the voltage Vh across the heater 28 is what is determined in step 4 of this subroutine, by selecting the input I7 of the A/D converter 53, and in the step 10 of this subroutine the calculation of the duty ratio D is performed by dividing the desired power Wh by the product of the actual voltage Vh and the actual amperage Ih. Apart from this feature, this third preferred embodiment functions in the same way as the first preferred embodiment, and the same advantages and benefits are obtained, as in the case of said first preferred embodiment described above. And, additionally, due to this special feature, if the battery voltage Vi should fluctuate, nevertheless accurate heater power control will be available. In other words, according to this third preferred embodiment, for yet more positive avoidance of heat surge problems, it is preferable to derive data relating to the power supplied to the heater by detecting the voltage being supplied across said heater as well as the current flowing through said heater, and in this case the power being dissipated by the heater can be positively determined.

Figure 13:
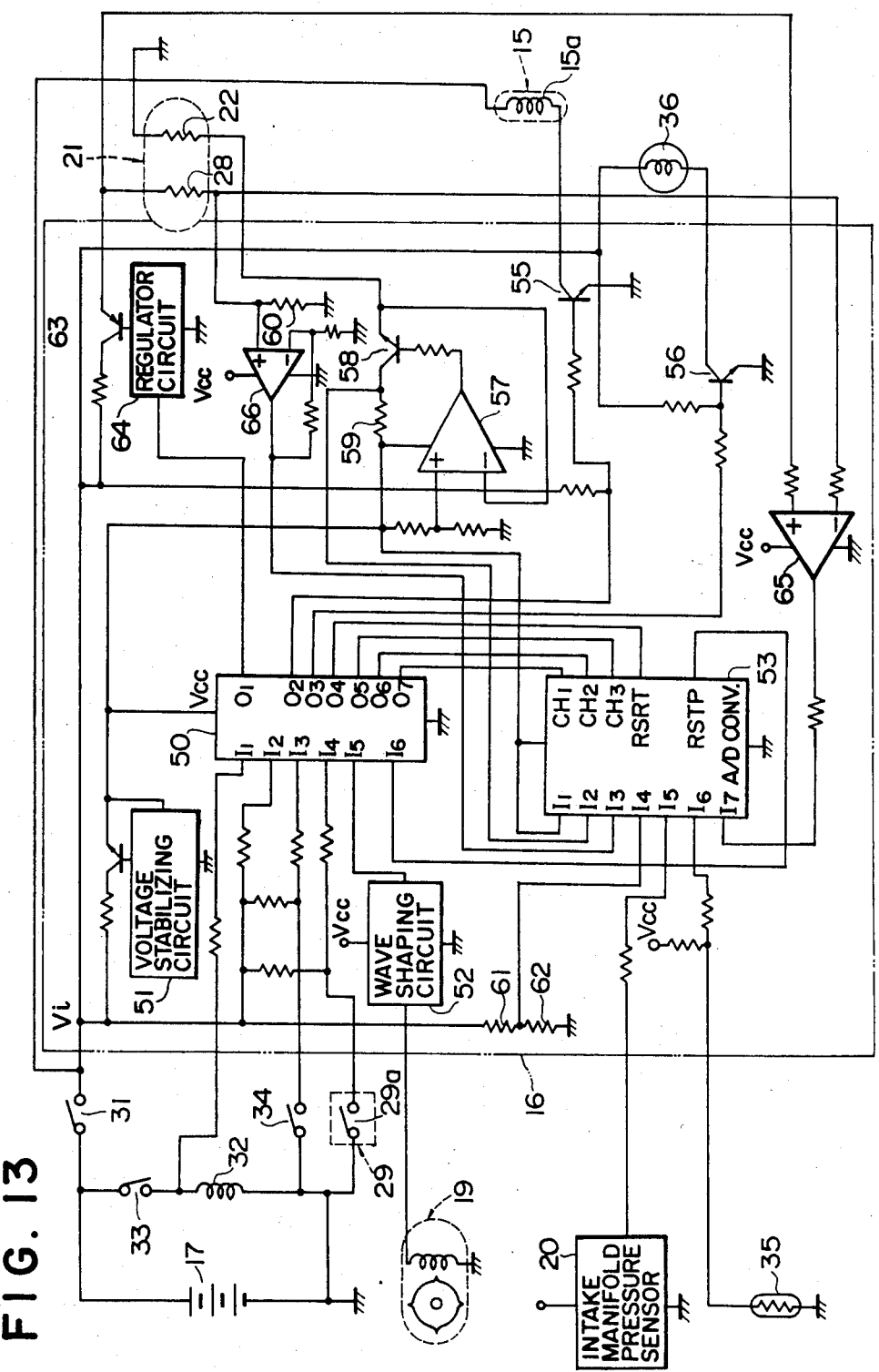
FIG. 13 is, similarly to FIGS. 3, 10, and 11 for the first through the third preferred embodiments, a partial circuit diagram of the fourth preferred embodiment of the oxygen sensor heating control system of the present invention, also showing various ancillary parts thereof, said fourth preferred embodiment combining the modifications of the second and the third preferred embodiments.

In FIG. 13 there is shown a partial circuit diagram of the control device 16 of a fourth preferred device embodiment of the present invention; and, again, reference symbols like to those used in FIGS. 1 through 12 correspond to like parts of the first through the third preferred embodiments. In this fourth preferred embodiment, the modifications of the second preferred embodiment of FIG. 10 and the third preferred embodiment of FIGS. 11 and 12 are incorporated together. In other words, the power supply to the heater element 28 is controlled by a transistor 63, the base of which is connected to the output of a regulator circuit 64, which is controlled from the output O1 of the microcomputer 50, and also the actual voltage supplied to said heater element 28 is measured by a differential amplifier 65, the output signal of which is sent to the input I7 of the A/D converter 53. Thus, again, the regulator circuit 64 receives a pulse signal from the output O1 of the microcomputer 50 which conveys information by its duty ratio, and produces a voltage signal corresponding to that duty ratio and supplies it to the base of the transistor 63. The flow chart of the subroutine of the microcomputer 50 in this fourth preferred embodiment corresponds to that of the subroutine of the third preferred embodiment whose flow chart is shown in FIG. 12, and hence is not particularly shown. Thus, this fourth preferred embodiment combines the advantages of the second and the third preferred embodiments. Otherwise, this fourth preferred embodiment functions in the same way as the first preferred embodiment, and the same advantages and benefits are obtained, as in the case of said first preferred embodiment described above.

Although the present invention has been shown and described with reference to the preferred embodiments thereof, and in terms of the illustrative drawings, it should not be considered as limited thereby. Various possible modifications, omissions, and alterations could be conceived of by one skilled in the art to the form and the content of any particular embodiment, without departing from the scope of the present invention. For example, although in the shown preferred embodiments the parameters according to which the fuel injection amount for the engine, and the amount of heater power provided for the oxygen sensor element heater, were engine intake manifold pressure and engine revolution speed, the present invention is not limited to this choice of parameters, and for example engine intake air flow and engine revolution speed could be utilized instead; other variations, such as throttle opening, are also possible for the chosen parameters. Therefore it is desired that the scope of the present invention, and of the protection sought to be granted by Letters Patent, should be defined not by any of the perhaps purely fortuitous details of the shown preferred embodiments, or of the drawings, but solely by the scope of the appended claims, which follow.

What is claimed is:

1. For an internal combustion engine comprising an exhaust system and an oxygen sensor fitted to said exhaust system, said sensor comprising a sensor element, an electrically powered resistive heater for heating said sensor element, and a source of electrical power to said heater:
    a method for controlling a value of electrical power supplied from the source to said heater, said method comprising the steps of:
    controlling the electrical power supplied to said heater according to engine operational parameters; and
    restricting the controlled electrical power supplied to said heater less than a predetermined maximum tolerable value when and only when said heater is not warmed to a predetermined active temperature.

2. A method according to claim 1, wherein said step of controlling the electrical power supplied to said heater comprises controlling the value of a current flowing continuously through said heater.

3. A method according to claim 1, wherein said step of controlling the electrical power supplied to said heater comprises supplying an intermittent voltage to said heater, said intermittent voltage having a duty factor; and controlling the duty factor of said intermittent voltage.

4. A method according to claim 1, wherein said step of controlling the electrical power supplied to said heater comprises detecting a current flowing through said heater to determine a value of power being supplied to said heater.

5. A method according to claim 1, wherein said step of controlling the electrical power supplied to said heater comprises detecting a voltage across said heater and a current flowing through said heater to determine a value of power being supplied to said heater.

6. A method according to claim 5, wherein said step of controlling the electrical power supplied to said heater comprises controlling a value of a current flowing continuously through said heater.

7. A method according to claim 5, wherein said step of controlling the electrical power supplied to said heater comprises supplying an intermittent voltage to said heater, said intermittent voltage having a duty factor; and controlling the duty factor of said intermittent voltage.

8. For an internal combustion engine comprising an exhaust system; an oxygen sensor fitted to said exhaust system, said oxygen sensor comprising a sensor element and an electrically powered heater for heating said sensor element; a source of electrical power connected to said heater; and a control system for controlling a value of electrical power supplied from said source to said heater, said control system comprising:
    means for detecting a value of electrical power supplied to said heater;
    means for determining a target value for the electrical power to be supplied to said heater according to engine operating parameters and for ensuring that the target value is less than a predetermined maximum tolerable value when and only when said heater is not warmed up to a predetermined operating temperature; and
    means for controlling a value of electrical power supplied to said heater to be substantially equal to said target value.

9. A system according to claim 8, wherein said means for controlling a value of electrical power supplied to said heater to be substantially equal to said target value comprises means for controlling a value of a current flowing continuously through said heater.

10. A system according to claim 8, wherein said means for controlling a value of electrical power supplied to said heater to be substantially equal to said target value comprises means for supplying an intermittent voltage to said heater, said intermittent voltage having a duty factor, and for controlling the duty factor of said intermittent voltage.

11. A system according to claim 8, wherein said means for detecting a value of electrical power supplied to said heater comprises means for detecting a value of current flowing through said heater.

12. A system according to claim 8, wherein said means for detecting a value of electrical power supplied to said heater comprises means for detecting a value of voltage across said heater and for detecting a value of current flowing through said heater.

13. A system according to claim 12, wherein said means for controlling a value of electrical power supplied to said heater to be substantially equal to said target value comprises means for controlling a value of a current flowing continuously through said heater.

14. A system according to claim 12, wherein said means for controlling a value of electrical power supplied to said heater to be substantially equal to said target value comprises means for supplying an intermittent voltage to said heater, said intermittent voltage having a duty factor, and for controlling the duty factor of said intermittent voltage.

* * * * *

UNITED STATES PATENT AND TRADEMARK OFFICE
CERTIFICATE OF CORRECTION

PATENT NO. : 4,611,562

DATED : September 16, 1986

INVENTOR(S) : J. Nakano, et al.

Page 1 of 3

It is certified that error appears in the above-identified patent and that said Letters Patent is hereby corrected as shown below:

ABSTRACT, line 18, change "over" to --overly--.

Column 1, line 30, change "rtio" to --ratio--.

Column 1, line 50, change "varies" to --varied--.

Column 1, line 64, after "constant" insert a comma.

Column 2, lines 55 and 56, change "sometimes the heater element voltage is" to --the heater element voltage is sometimes restricted--.

Column 2, line 57, omit "is" between "This" and "means".

Column 3, line 25, change "provides" to --provide--.

Column 3, line 55, change "that" to --wherein--.

Column 3, line 57, change "should be" to --is--.

Column 4, line 17, change "as well of" to --as well as of--.

Column 4, line 29, after "preferable" insert a comma.

UNITED STATES PATENT AND TRADEMARK OFFICE
CERTIFICATE OF CORRECTION

PATENT NO. : 4,611,562
DATED : September 16, 1986
INVENTOR(S) : J. Nakano, et al.

It is certified that error appears in the above-identified patent and that said Letters Patent is hereby corrected as shown below:

Column 4, lines 45-48, change "Accordingly, it is as much as possible prevented that during initial engine warming up operation the quality of the exhaust emissions of the engine should be poor." to --Accordingly, the occurrence of poor quality exhaust emissions during initial engine warming up operation is prevented to the greatest extent possible.--.

Column 6, lines 51-52, change "only a portion of an exhaust manifold 8 incorporated in which is shown." to --of which only a portion of an exhaust manifold 8 incorporated therein is shown.--.

Column 6, line 63, after "which" insert a comma, and after "control" insert a comma.

Column 7, line 52, change "earthing" to --grounding--.

Column 8, line 3, delete "and so on".

Column 11, line 25, change "heater ON." to --heater 28 ON.--.

UNITED STATES PATENT AND TRADEMARK OFFICE
CERTIFICATE OF CORRECTION

PATENT NO. : 4,611,562

DATED : September 16, 1986

INVENTOR(S) : J. Nakano, et al.

It is certified that error appears in the above-identified patent and that said Letters Patent is hereby corrected as shown below:

Column 14, line 6, after "figure" insert a comma, and omit the word "to".

Column 14, line 8, after "embodiment" inser a comma.

Column 14, line 10, omit the comma after "FIG. 3".

Column 14, line 30, omit the word "to", insert a comma after "like", and insert a comma after "10".

Column 14, line 41, after "ment" insert a comma, and after "FIG. 5" insert a comma.

Column 14, line 67, insert a comma after "symbols", omit the word "to", and insert a comma after "12".

Column 15, line 67, insert --to-- after "heater".

Signed and Sealed this

Fourteenth Day of April, 1987

Attest:

DONALD J. QUIGG

Attesting Officer     Commissioner of Patents and Trademarks